United States Patent [19]
Chokai et al.

[11] Patent Number: 5,589,477
[45] Date of Patent: Dec. 31, 1996

[54] PYRIMIDINE DERIVATIVES AND DRUGS

[75] Inventors: Shoichi Chokai, Kyoto; Tomiyoshi Aoki, Shiga; Kiyoshi Kimura, Osaka, all of Japan

[73] Assignee: Nippon Shinyaku Company, Limited, Japan

[21] Appl. No.: 983,515

[22] PCT Filed: Aug. 29, 1991

[86] PCT No.: PCT/JP91/01152

§ 371 Date: Feb. 26, 1993

§ 102(e) Date: Feb. 26, 1993

[87] PCT Pub. No.: WO92/04333

PCT Pub. Date: Mar. 19, 1992

[30] Foreign Application Priority Data

Aug. 31, 1990 [JP] Japan ................................. 2-231029
May 29, 1991 [JP] Japan ................................. 3-155628

[51] Int. Cl.$^6$ ................. A61K 31/505; C07D 403/04; C07D 403/12
[52] U.S. Cl. ............. 514/256; 514/222.2; 514/222.8; 514/269; 544/3; 544/55; 544/59; 544/69; 544/295; 544/296; 544/319; 544/326
[58] Field of Search ............. 544/3, 55, 58.6, 544/59, 63, 295, 296, 319, 326; 514/256, 269, 222.2, 228.8

[56] References Cited

U.S. PATENT DOCUMENTS

| | | | |
|---|---|---|---|
| 3,787,411 | 1/1974 | Ruschig et al. | 544/359 |
| 4,493,726 | 1/1985 | Burdeska et al. | 71/87 |
| 4,725,600 | 2/1988 | Takaya et al. | 514/269 |

OTHER PUBLICATIONS

Thompson et al. New England Journal of Medicine, 323, pp. 445–448, 1990.
Pomora et al. Alan R. Liss, Inc., Alzheimer's Disease and Related Disorders, pp. 1223–1233, 1989.
Gray te al. Trends in Pharmacological Sciences, pp. 85–89, 1989.
Quirion et al. Trends in Pharmacological Sciences, pp. 80–84, 1989.
D. Collerton, "Cholinergic Function and the Intellectual Decline in Alzheimer's Disease", published in *Neuroscience*, vol. 19, No. 1, pp. 1–28 (1986).
Brown et al. —Chem Abst., 100, No. 28; 2097334, 1984.
Abstract of Japanese 40/15197, 1965.
Brown et al. Aust. J. Chem., 37(11, pp. 155–163 1984).

*Primary Examiner*—Yogendra N. Gupta
*Attorney, Agent, or Firm*—Graham & James LLP

[57] ABSTRACT

The object of the present invention is to obtain new class of compounds which have improving effect on learning and memory disorders with good selectivity in central nervous system and little side effects and then to provide a good medicine for treatment of dementia.

The present invention relates to the compounds represented by the following general formula or their pharmacologically acceptable salts and the drugs of improving learning or memory disorders comprising them as active ingredients.

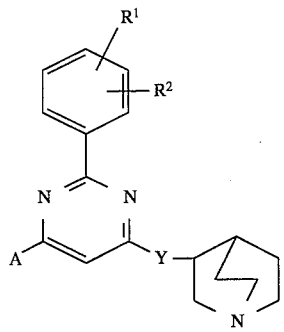

(wherein $R^1$ and $R^2$ are the same or different and are hydrogen, hydroxy, alkoxy, trifluoromethyl or halogen. A represents methyl, trifluoromethyl, or tert-butyl. Y represents O or NH.)

24 Claims, No Drawings

PYRIMIDINE DERIVATIVES AND DRUGS

TECHNICAL FIELD

This invention relates to pyrimidine derivatives and their pharmacologically acceptable salts represented by the following general formula [I].

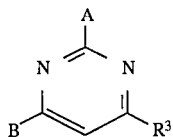

[I]

wherein A and B are as follows: When A represents

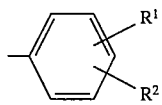

B represents methyl, trifluoromethyl, or tert-butyl; When B represents

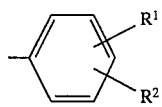

A represents methyl, trifluoromethyl, or tert-butyl. $R^1$ and $R^2$ are the same or different and each is a hydrogen atom, a hydroxy group, an alkoxy group, trifluoromethyl or halogen. $R^2$ represents (1), (2) or (3), represented by the following formulas.

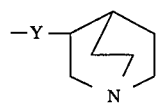

(1)

wherein Y represents O or NH.

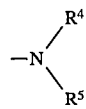

(2)

wherein $R^4$ and $R^5$ represent the following (a) or (b).
(a) $R^4$ and $R^5$ are the same or different and each is hydrogen or alkyl group.
(b) $R^4$ and $R^5$ link to form piperazino which is substituted with an aryl group or an aralkyl group.

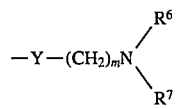

(3)

wherein Y represents O or NH. m is 2 or 3. $R^6$ and $R^7$ are the same or different and each is a hydrogen atom or an alkyl group, or form a 5 to 6 membered cyclic-amino group with the adjacent nitrogen atom. These cyclic-amino groups may include another nitrogen, oxygen or sulfur atom, and moreover, those may be substituted with an aryl group with or without substituent(s), an aralkyl group with or without substituent(s), or an aroyl group with or without substituent(s).

Since the compounds of the present invention have improving effect on learning and memory disorders with low toxicity as described later, those are useful as remedies for dementia etc.

BACKGROUND ART

According with the aging of the population, dementia have been a dominant disease in the medication of the elderly patients. However, the remedies for the treatment of dementia have not been established. Cerebral metabolism enhancers, cerebral blood flow improving agents, tranquilizers. cholinomimetic agents and the like have been tried to use for the treatment. However, the effect of these agents are not reproducible and insufficient. Therefore, better remedies for treatment have been required.

In the dementia of alzheimer type, a type of senile dementia, various nervous systems are damaged. Especially, it has been reported that cholinergic nervous systems, which play important roles in learning and memory functions, are significantly damaged. Therefore, the development of central acethylcholinergic neuron enhancers have been an large stream of development in the improving agents for learning and memory disorders. As for the acethylcholinergic neuron enhancers, precursors (such as choline and lecithin), choline esterase inhibitors or muscarinic agonists have been developed so far. However, they are not satisfactory enough.

On the other hand, various kinds of pyrimidine derivatives have been reported.(for example, CA 93:45871w, 97:158036d, 98:34562y, 100:209733u, 101:110856v, 102:162193s, 104:47176t, 107:236641p, 109:92924z and so forth). It is described in CA 100:209733u that the phleomycin amplifying effect of the compounds which have similar structures to the compounds of the present invention. Also in CA 104:47176t, it is described that the plant's growth regulating effect of the compounds which have similar structures to the compounds of the present invention.

However, up to this point, there have been no literatures describing that the compounds of the present invention and analogous pyrimidine derivatives have improving effects on learning and memory disoders.

DISCLOSURE OF THE INVENTION

The inventors have studied in order to obtain the compounds which are superior to the conventionally known drugs for learning and memory disorders in point of effectiveness, safety and durability.

Accordingly, the object of the present invention has been to obtain new compounds which have improving effect on learning and memory disorders with good selectivity in central nervous system and little side effects and then to provide a good medicine for the treatment of dementia.

The gist of the present invention is in the chemical structure of the compound itself which is represented by a general formula [I]. These are not only new compounds which are not yet described in any literatures so far, but also showing good pharmacological effects with low toxicity as described later. However, the following compounds such as (i) to (x), as described above, are known compounds which are already reported in literatures.

However, in also these compounds, their excellent improving effects on learing and memory disorder have been found for the first time by the inventors. Therefore, these compounds are also included in the present invention as the improving agents for learning and memory disorders.

(i) The compound wherein A is phenyl, B is methyl and $R^3$ is

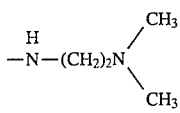

(ii) The compound wherein A is phenyl, B is methyl and $R^3$ is

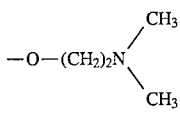

(iii) The compound wherein A is methyl, B is phenyl and $R^3$ is

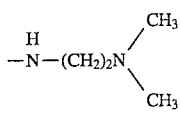

(iv) The compound wherein A is methyl, B is phenyl and $R^3$ is

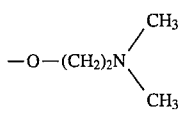

(v) The compound wherein A is methyl, B is phenyl and $R^3$ is

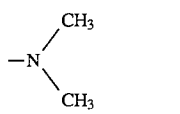

(vi) The compound wherein A is methyl, B is phenyl and $R^3$ is —$NH_2$.

(vii) The compound wherein A is methyl, B is 4-chlorophenyl and $R^3$ is —$NH_2$.

(viii) The compound wherein A is methyl, B is 4-methoxyphenyl and $R^3$ is —$NH_2$.

(ix) The compound wherein A is phenyl, B is methyl and $R^3$ is —$NH_2$.

(x) The compound wherein A is 4-chlorophenyl, B is methyl and $R^3$ is —$NH_2$.

In the general fomula [I], as the alkoxy group represented by $R^1$ and $R^2$, it is preferable to be straight or branched chain having 1 to 4 carbon atoms and illustrative of such alkoxys are methoxy, ethoxy, n-propoxy, isopropoxy, n-butoxy, isobutoxy or sec-butoxy and so forth. The examples of the halogens are chlorine, fluorine, bromine, iodine and the like.

As the alkyl groups represented by $R^4$ and $R^5$ it is preferable to be straight or branched chain having 1 to 4 carbon atoms. And examples of the alkyl are methyl, ethyl, n-propyl, isopropyl, n-butyl, isobutyl, sec-butyl and the like.

As the aryl group which is a substituent of piperazino moiety represented by —$NR^4R^5$, it is preferable to be ones having 6 to 12 carbon atoms. And examples of the aryl are phenyl, α-naphthyl, β-naphthyl, biphenyl and so on, which is un-substituted or substituted with alkoxy group.

As the aralkyl groups, it is preferable to be ones having 7 to 14 carbon atoms. And examples of the aralkyl are benzyl, phenetyl, 3-phenylpropyl, naphthylmethyl, diphenylmethyl and so on, which is un-substituted or substituted with halogen(s).

As the alkyl groups represented by $R^6$ and $R^7$, it is preferable to be ones described above.

As the 5 to 6 membered cyclic amino groups represented by —$NR^6R^7$, it is preferable to be ones such as pyrrolidino, piperidino, piperazino, morpholino and thiomorpholino. As the aryl or aralkyl groups as the substituent group of the cyclic amino moiety, it is preferable to be ones described above.

As the aroyl group, benzoyl un-substituted or substituted with alkoxy(ies) or halogen(s) is preferable.

Any reference to the compounds of the present invention, in addition to the examples of compounds related to the process for production described later, there may be also mentioned the following examples of compounds.

4-[2-[4-[bis(4-fluorophenyl)methyl]piperazino]ethoxy]-6-methyl-2-phenylpyrimidine 4-[2-(4-diphenylmethylpiperazino)ethoxy]-2-phenyl-6-trifluoromethylpyrimidine 4-[2-[4-[bis(4-fluorophenyl)methyl]piperazino]ethoxy]-2-phenyl-6-trifluoromethylpyrimidine 4-[2-(4-diphenylmethylpiperazino)ethoxy]-2-(4-fluorophenyl)-6-trifluoromethylpyrimidine 4-[2-[4-[bis(4-fluorophenyl)methyl]piperazino]ethoxy]-2-(4-fluorophenyl) 6-trifluoromethylpyrimidine 4-[2-(4-diphenylmethylpiperazino)ethoxy]-2-(4-trifluoromethylphenyl) 6-trifluoromethylpyrimidine 4-[2-[4-[bis(4-fluorophenyl)methyl]piperazino]ethoxy]-2-(4-trifluoromethylphenyl) 6-trifluoromethylpyrimidine 4-(1-azabicyclo[2,2,2]octo-3-yloxy)-2-phenyl-6-trifluoromethylpyrimidine 4-(1-azabicyclo[2,2,2]octo-3-yloxy)-6-tert-butyl-2-(4-trifluoromethylphenyl)pyrimidine 4-(1-azabicyclo[2,2,2]octo-3-ylamino)-2-(4-methoxyphenyl)-6-methylpyrimidine 4-(1-azabicyclo[2,2,2]octo-3-ylamino)-2-(4-fluorophenyl)-6-methylpyrimidine 4-(1-azabicyclo[2,2,2]octo-3-ylamino)-2-(4-trifluoromethylphenyl)-5-methylpyrimidine The compounds of the present invention can be produced for example, by the following methods.

Method A: When $R^3$ is

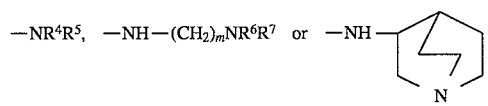

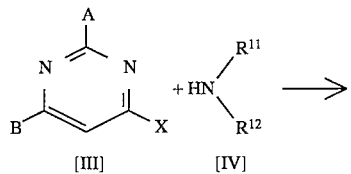

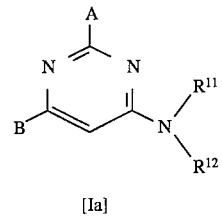

(Wherein, A and B are the same as the defined above, X is halogen. $HNR^{11}R^{12}$ represents $HNR^4R^5$, $H_2N(CH_2)_m NR^6R^7$ or

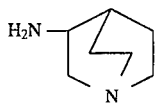

$R^4$–$R^7$ and m are the same as the defined above.)

Method B: When $R^3$ is $-O-(CH_2)_m NR^6R^7$ or $-O-$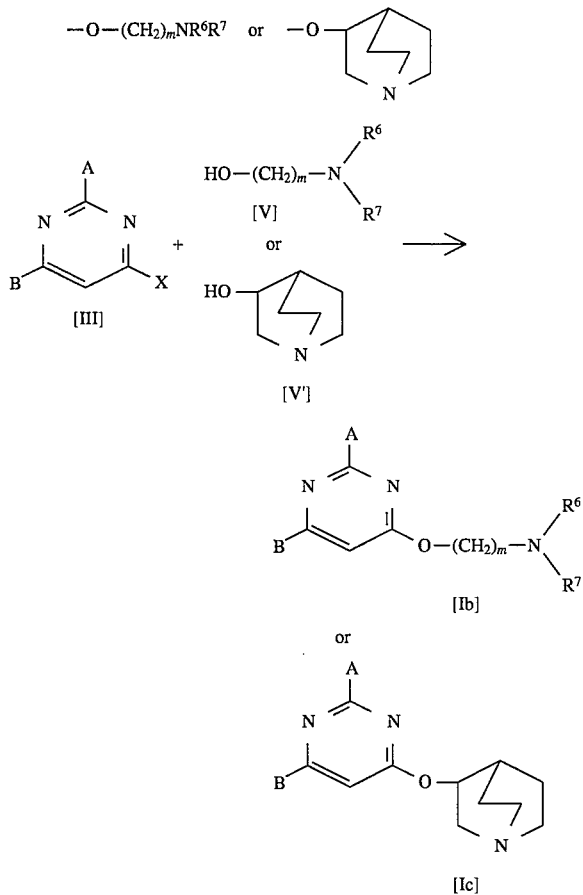

(wherein, A, B, X, $R^6$, $R^7$ and m are the same as the defined above.)

Method C: When $R^3$ is $-O-(CH_2)_m NR^6R^7$ or

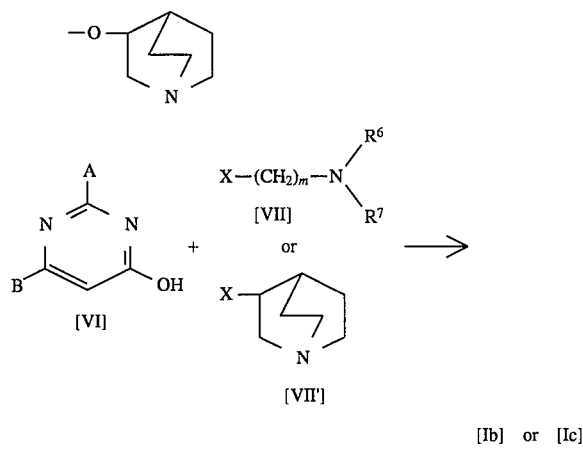

(wherein A, B, X, $R^6$, $R^7$ and m are the same as the defined above.)

Method A

[Ia] can be produced by the reaction of halogenopyrimidine [III] with amine [IV] in an inert solvent, in the presence of a base at 30° to 120° C., preferably 60° to 80° C.

As the reaction solvents, an aprotic polar solvent such as acetonitrile, dimethylsulfoxide, and N,N-dimethylformamide (DMF), alcohols such as methanol, ethanol and isopropanol, ethers such as tetrahydrofuran, dimethoxyethane, diethylether and dioxane, glimes such as methylcellosolve and ethyleneglycol dimethylether, halogenated hydrocarbons such as methylene chloride and chloroform, hydrocarbons such as benzene, toluene and xylene, or the mixture of these solvents can be used.

As the bases, alkali carbonates (for example, potassium carbonate, sodium carbonate etc.), alkali bicarbonates (for example, potassium bicarbonate, sodium bicarbonate etc.), inorganic salts of alkali hydroxides (for example, potassium hydroxide, sodium hydroxide etc.) or excess amines ($HNR^{11}R^{12}$) can be used.

The reaction time is usually 4 to 24 hours, although it may vary depending on the kind of starting materials, bases and solvents used.

The amount of amine [IV] is preferably 1 to 1.2 moles per 1 mole of [III].

Method B

Either [Ib] or [Ic] can be produced by the reaction of halogenopyrimidine [III] with hydroxyalkylamine [V] or quinuclidiol [V'] in an inert reaction solvent, in the presence of a catalyst at 0° to 80° C., preferably 10° to 30° C.

As the reaction solvents, N,N-dimethylformamide (DMF) or ethers such as tetrahydrofuran, dimethoxyethane, diethylether, dioxane, diethyleneglycol and dimethylether, or the mixture of these solvents can be used. As the catalysts, sodium hydride, sodium amide, potassium-tert-butoxide, butyllithium and the like can be used.

The reaction time is usually 2 to 24 hours although it may vary depending on the kind of starting materials, solvents and catalysts used.

The amount of hydroxyalkylamine [V] or quinuclidiol [V'] is preferably 1 to 1.2 moles per 1 mole of [III].

Method C

[Ib] or [Ic] can be produced by the reaction of hydroxypyrimidine [VI] with halogenoalkylamine [VII] or halogenoquinuclidine [VII'] in a solvent which is mentioned in method A, in the presence of a base at 0° to 80° C.

As the bases, sodium hydride, potassium carbonate, sodium hydroxide, potassium hydroxide and the like can be used.

The reaction time is usually 2 to 10 hours although it may vary depending on the kind of starting materials, bases and solvents used.

The amount of halogenoalkylamine [VII] or halogenoquinucridine [VII'] is preferably 1 to 1.2 moles per 1 mole [VI].

The starting materials of [III] and [IV], which are described in detail as the reference examples, can be produced as follows.

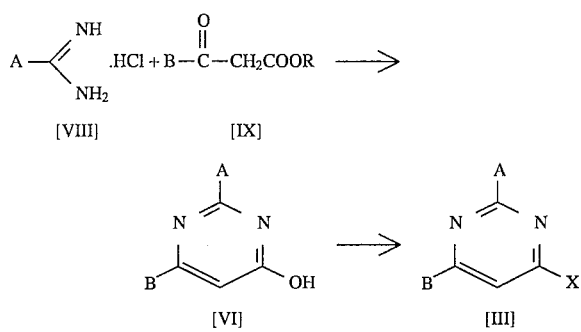

(wherein A, B and X are the same as defined above. R is a lower alkyl.)

[VI] can be produced by the reaction of amidine [VII] with acylacetic acid ester [IX] in the presence of a base (inorganic salts such as potassium carbonate and sodium carbonate, or organic salts such as triethylamine), in an inert solvent (for example, alcohols such as methanol and ethanol, aprotic solvents such as acetonitrile and N,N-dimethylformamide.) at 60° to 140° C. for 5 to 24 hours. In addition, [III] can be prepared by heat-refluxing this with phosphorus oxychloride for 10 minutes to 1 hour.

Although there are some compounds in the present invention which possess asymmetric carbons, both optical isomers of each compound and their racemic mixtures are included in the present invention. The optical isomers can be obtained by optically resolution of their racemic mixtures based upon their basicity with the use of optical active acids (such as tartaric acid, dibenzoyltartaric acid, mandelic acid 10-camphor-sulfonic acid) according to conventional methods, or by using optically active compounds, [IV], [V'] and [VII'] prepared previously as raw materials.

The desired compound [I] produced by this manner can be isolated and purified in the form of free base or acid additional salt, for example, by concentration, change of liquid property, transference of solute, solvent extraction, crystallization, fractional distillation, chromatography etc. according to the known method per se.

The acid additional salts can include the salts of mineral acids such as hydrochloric acid, hydrobromic acid, sulfuric acid, nitric acid and phosphoric acid, and the salts of organic acids such as acetic acid, citric acid tartaric acid, maleic acid, succinic acid, fumaric acid, p-toluenesulfonic acid, benzenesulfonic acid and methanesulfonic acid.

When the compounds of the present invention are given as medicines, those are administered to animals including human, as it is or as pharmaceutical compositions which contains the compounds for the concentration of, for example, 0.1 to 99.5%, preferably 0.5 to 90% in pharmaceutically acceptable carriers which are nontoxic and inert.

As the carriers, more than one kind of diluents, filling materials and other supplementary substances for prescription in the forms of solid, semi-solid or liquid states are used. It is preferable that pharmaceutical compositions are administered as a unit dosage form. The pharmaceutical compositions of the present invention can be administered orally, intra-tissue, locally (such as percutaneous administration etc.) or per rectum. It is the matter of course that those should be administered in suitable form depending on the way of administration.

Although it is preferable that the doses as the improving agents for learning and memory disorders should be controlled considering the patient's condition such as age and body weight and so on, administration route, and disposition and degree of the diseases etc., it is general ranges that one-day dose of the effective constituent in the present invention for adults is usually 0.1 mg to 1 g/human, preferably 1 to 300 mg/human. Depending on the cases, sometimes the dose below the above dose range is enough, or contrary, some requires more dose than the range. It is also preferable to administer in divided doses by 2 to 4 times a day.

Oral administration can be carried out using solid or liquid unit dosage such as fine powder, powder formulations, tablets, sugar-coating drugs, capsules, granules, suspensions, liquid preparations, syrups, drops, sublingual tablets and other formulations.

Fine powders are produced by pulverizing the active substances to be adequately fine. Powder formulation are prepared by pulverizing the active substances to be adequately fine and admixing with similarly pulverized pharmaceutical carriers, for example, edible carbohydrates such as starch or mannitol, and the others. If necessary, it may be admixed with flavoring agents, preservatives, dispersing agents, coloring agents, perfume and the others.

Capsules are produced by filling fine powders or powder formulation which are previously pulverized as the mentioned above, or granulated substances as mentioned in the section of tablets, into capsule integuments such as gelatin capsule. The pulverized substances are admixed with lubricants or fluidifying agents such as colloidal silica, talc, magnesium stearate and potassium stearate as well as solid polyethyleneglycol, and then the filling procedure can be carried out. The effectiveness of drugs when the capsule is taken can be improved, if disintegrators or solubilizing agents such as carboxymethylcellulose, calcium carboxymethyl cellulose, lower substituted hydroxypropyl cellulose, sodium croscarmellose, sodium carboxymethyl starch, calcium carbonate and sodium carbonate are added into the powder.

Moreover, soft capsule can be prepared by suspending and dispersing the fine powder of this product in vegetable oil, polyethyleneglycol, glycerin or surfactants and then wrapping this with gelatin sheets. Tablets can be produced the way that powdery mixtures is prepared by adding filler, then it is granulated or slugged, and then compressed after addition of disintegrator or lubricant. The powder mixtures are prepared by admixing the suitably pulverized substance with the above mentioned diluents and bases, and if necessary, binders (for example, sodium carboxymethylcellulose, methylcellulose, hydroxypropylmethylcellulose, gelatin, polyvinylpyrolidone, polyvinylalcohol and the like), reabsorbing agents (for example, quaternary salts) and adsorbing agents (for example, bentonite, kaolin, dicalcium phosphate and the like) may be used simultaneously in this procedure. The powdery mixture can be changed to granule by the way that first it is moistened with binders, for example, syrup, starch paste, acacia, cellulose solution or high polymer solution, and then it is stirred to mix, dried and pulverized. In stead of granulating the powder in this way, it is possible to make granule by pulverizing the incomplete form of slug which is obtained after the previous compression by the compressor.

The granule made by this way can be prevented from mutual adhering by adding lubricants such as stearic acid, stearate, talk and mineral oil. The mixture lubricated in this way is subsequently compressed. The bare tablets made in this manner can be given film-coating or sugar-coating.

The drugs may be directly compressed after mixing with fluid inactive carrier without the process of granulation and slugging. The transparent or semitransparent protecting film which is consisted of sealing-up film made from shellac, the film made from sugar and high polymer, and the things like rubbing-up film consisted of wax can also be used.

Other oral dosage formulation such as solutions, syrups and elixirs can be also made as unit dosage form which contain a constant dose of drug in a constant amounts of the formulation. Syrups are produced by dissolving compounds in suitable perfumed water and elixirs are produced by using nontoxic alcohol carriers. Suspensions is prescribed by dispersing a compound in nontoxic carriers. It is also possible to add solubilizing agents or emulsifying agents (for example, ethoxylated-isostearylalcohols or polyoxyethylenesorbitol esters), preservatives, flavoring agents (for example, peppermint oil or saccharin) and the others, when required.

If necessary, the prescription of unit dosage for oral administration may be as microcapsulated formulation. The said prescription can also provide prolongation of action time and lasting release of drugs by film-coating and filling up into high polymer wax and the like.

Intra-tissue administrations can be carried out using liquid unit dosage form, such as the form of solution and suspension which are prepared for subcutaneous, intramuscular or intravenous injections. These formulations are produced by the way that a certain amount of compound is suspended or dissolved in nontoxic liquid carriers such as aqueous or oily vehicles which are suitable for the purpose of injection, and then the said suspension or solution is sterilized. Nontoxic salts or the salt-solution may be added to them in order to isotonize the injections. In addition, stabilizers, preservatives, emulsifiers and the like can be used at the same time with them.

Rectal administration can be carried out using suppositories and the likes which are produced by dissolving or suspending compounds in water-soluble or insoluble solids with low melting point, for example, polyethyleneglycol, cacao butter, semisynthetic fats and oils (such as witepsol, a registered trademark), higher esters (such as myristilpalmitate) and their mixture.

THE BEST MODE FOR PRACTICING THE INVENTION

The present invention will be further illustrated by giving reference examples, examples, test examples and pharmaceutical examples of the compound of the present invention hereinafter.

Reference Example 1

Preparation of 4-hydroxy-2-(4-methoxyphenyl)-6-methylpyrimidine (1) Preparation of 4-methoxybenzimidic acid methylester hydrochloride 25 g of anisonitril was dissolved in 250 ml of methanol. After saturation with hydrogen chloride gas under cooling in ice-water and stirring, the solution was stirred at room temperature for 15 hours. Then, methanol was evaporated in vacuo. Ether was added to the residue and the crystals were filtered off and dried. Whereby 35.9 g of the desired substance was obtained as white crystals. Melting point is 111° to 112° C. (Decomposition).

(2) Preparation of 4-methoxybenzamidine hydrochloride 35.9 g of 4-methoxybenzimidic acid methylester hydrochloride was dissolved in 300 ml of methanol. After saturation with ammonia gas under cooling in ice-water and stirring, the solution was stirred at room temperature for 15 hours. Then, methanol was evaporated in vacuo. Ethyl acetate was added to the residue. The precipitated crystals were filtered off and dried. Whereby 30.9 g of the desired substance was obtained as white crystals. Melting point is 220° to 221° C.

(3) Preparation of 4-hydroxy-2-(4-methoxyphenyl)-6-methylpyrimidine

To the mixture of 10 g of 4-methoxybenzamidine hydrochloride, 7.7 g of ethyl acetoacetate and 16.3 g of potassium carbonate were added 120 ml of ethanol, and the mixture was heat-refluxed with stirring for 7 hours. The reaction mixture was cooled and filtered to remove insoluble substances. The filtrate was evaporated. Water was added to the residue to dissolve and then the resulting solution was neutralized with acetic acid. The precipitated crystals were filtered off, washed with water and dried. Whereby 10.9 g of the desired substance was obtained as white crystals. Melting point is 202° to 203° C.

In the same way, the following compounds were obtained.

2-(4-fluorophenyl)-4-hydroxy-6-methylpyrimidine. Melting point is 224° to 225.5° C.

4-hydroxy-2-(4-methoxyphenyl)-6-trifluoromethylpyrimidine. Melting point is 239° to 240.5° C.

4-hydroxy-6-methyl-2-(4-trifluoromethylphenyl)pyrimidine. Melting is point 222° to 224° C.

Reference Example 2

Preparation of 4-chloro-2-(4-methoxyphenyl)-6-methylpyrimidine 6.5 g of 4-hydroxy-2-(4-methoxyphenyl)-6-methylpyrimidine prepared in reference example 1 (3) was added to 30 ml of phosphorus oxychloride, and the mixture was refluxed with stirring for 30 minutes. The reaction mixture was cooled and poured into diluted ammonia solution and the precipitated crystals were filtered off. The crystals were dissolved in chloroform. After the chloroform layer was washed twice with water, it was dried with anhydrous magnesium sulfate and was evaporated in vacuo. The residue was crystallized with n-hexane and filtered off. Whereby 5.1 g of crystals was obtained. Melting point is 80° to 81° C.

In the same way, the following compounds were obtained.

4-chloro-2-(4-fluorophenyl)-6-methylpyrimidine. Melting point is 87° to 88.5° C.

4-chloro-2-(4-methoxyphenyl)-6-trifluoromethylpyrimidine. Melting point is 54° to 56° C.

4-chloro-6-methyl-2-(4-trifluoromethylphenyl)pyrimidine. Melting point is 66° to 67° C.

Reference Example 3

Preparation of 4-hydroxy-6-(4-methoxyphenyl)-2-methylpyrimidine 1.89 g of acetamidine hydrochloride and 4.44 g of etyl paramethoxybenzoylacetate were dissolved in 40 ml of ethanol. After addition of 5.52 g of potassium carbonate, the solution was refluxed with stirring for 8 hours, and then evaporated in vacuo. 5 g of sodium hydroxide was dissolved in 30 ml of water and this was added to the evaporated residue. Add ether, then extract, the aqueous layer was neutralized with acetic acid. The resulting precipitations were filtered off, washed with water and dried. Then 1.1 g of crystals were obtained. Melting point is 270° to 272° C.

Reference Example 4

Preparation of 4-chloro-6-(4-methoxyphenyl)-6-methylpyrimidine 9 g of 4-hydroxy-6-(4-methoxyphenyl)-2-methylpyrimidine was added to 60 ml of phosphorus oxychloride and the mixture was refluxed with stirring for 30 minutes. The reaction mixture was added to diluted ammonia solution little by little, and the precipitate was filtered. This was dissolved in chloroform and washed with potassium carbonate solution. After washing, the chloroform layer was dried with anhydrous magnesium sulfate and evaporated in vacuo. The residue was crystallized with n-hexane and filtered off. Whereby 5.78 g of the crystals were obtained. Melting point is 65° to 67° C.

EXAMPLE 1

4-(1-azabicyclo[2,2,2]-octo-3-yloxy)-2-(4-methoxyphenyl)-6-methylpyrimidine maleate 15.0 g of 4-chloro-2-(4-methoxyphenyl)-6-methylpyrimidine and 8.13 g of 3-quinuclidinol were dissolved in 150 ml of N,N-dimethylformamide. Then 2.56 g of 60% sodium hydride was added to the solution under ice-cooling and stirring. After stirring for 2 hours under ice-cooling and additionally for 5 hours at room temperature, the reaction mixture was poured into ice-water and the oily substance was extracted with ethyl acetate. After the ethyl acetate layer was washed twice with water, it was dried with anhydrous magnesium sulfate and evaporated in vacuo. The residue was applied to a column chromatography with silica gel (Wako gel C-200 500 g, elution with chloroform and 3% methanol-chloroform in order), then 16.9 g of oily substance was obtained. This was dissolved in 100 ml of methanol, methanol solution of 6.0 g of maleic acid was added. After stirring, the solution was evaporated in vacuo. Ether was added to the residue to crystallize then the crystals were filtered off. Whereby 16.4 g of the crystals were obtained. These were recrystallized with ethanol, whereby 12.6 g of the crystals were obtained. Melting point is 163° to 164° C.

Elementary analysis for ($C_{19}H_{22}N_3O_2 \cdot C_4H_4O_4$ 441.48)

Calculated (%) C:62.57 H:6.16 N:9.52

Found (%) C:62.51 H:6.40 N:9.61

EXAMPLE 2

(R)-(-)-4-(1-azabicyclo[2,2,2]octo-3-yloxy)-2-(4-methoxyphenyl)-6-methylpyrimidine maleate 1 g of 4-chloro-2-(4-methoxyphenyl)-6-methylpyrimidine was dissolved in tetrahydrofuran 15 ml and DMF 10 ml. After addition of 542 mg of (R)-(+)-3-quinuclidinol thereto, 340 mg of 60% sodium hydride was added to the solution under ice-cooling and stirring. After stirring for 2 hours under ice-cooling and additionally for 17 hours at room temperature, the reaction mixture was poured into ice-water and extracted with ethyl acetate. After the ethyl acetate layer was extracted with diluted hydrochloride solution, the aqueous layer was neutralized with an aqueous sodium hydroxide solution. Then this was extracted with ethyl acetate. After washing the ethyl acetate layer with water and drying with anhydrous magnesium sulfate, the solvent was evaporated in vacuo. The resulting yellow crystals were purified with column chromatography with silica gel(Wako gel C-200 20 g, elution with chloroform and 3% methanol-chloroform in order), then 590 mg of white crystals were obtained.

After the crystal was dissolved in methanol and added maleic acid 211 mg/methanol 2 ml, ether was added and the precipitated crystals was filtered off. This was recrystallized with acetonitrile/ether mixed solution. Whereby 624 mg of the desired compound was obtained as white crystal. Melting point is 158.5° to 159.5° C.

Elementary analysis for ($C_{19}H_{23}N_2O_2 \cdot C_4H_4O_4$)

Calculated (%) C:62.57 H:6.16 N:9.52

Found (%) C:62.88 H:6.16 N:9.52

Specific rotation $[\alpha]_D$ (20° C.)=−33.2 (c=1, $H_2O$)

EXAMPLE 3

4-[2-(4-diphenylmethylpiperazino)ethoxy]-2-(4-methoxyphenyl)-6-methylpyrimidine 0.6 g of 4-chloro-2-(4-methoxyphenyl)-6-methylpyrimidine and 0.76 g of 1-diphenylmethyl-4-(2-hydroxyethyl)piperazine were dissolved in 20 ml of dried tetrahydrofuran. After addition of 0.1 g of 60% sodium hydride, the mixture was stirred for 20 hours at room temperature. The reaction mixture was poured into ice-water and was extracted with ethyl acetate. After the extract was washed with water and was dried with anhydrous magnesium sulfate, then was evaporated in vacuo. The resulting residue was purified with column chromatography with silica gel (Wako gel C-200, elution with chloroform and then chloroform:ethyl acetate= 8:1). The desired fraction was crystallized by evaporating the solvent under reduced pressure. The crystals were recrystallized with the solvent mixed with chloroform and ether, resulting to obtain 0.6 g of crystals. Melting point is 132° to 133° C.

Elementary analysis for ($C_{31}H_{34}N_4O_2$)

Calculated (%) C:75.28 H:6.93 N:11.33

Found (%) C:74.95 H:7.03 N:11.24

EXAMPLE 4

4-(4-diphenylmethylpiperazino)-2-(4-methoxyphenyl)-6-methylpyrimidine 1.17 g of 4-chloro-2-(4-methoxyphenyl)-6-methylpyrimidine and 1.38 g of 1-diphenylmethylpiperazine were dissolved in 20 ml of N,N-dimethylformamide. After the addition of 1 g of potassium carbonate, the mixture was stirred for 6 hours at 80° to 85° C. The reaction mixture was poured into ice-water, then the resulting crystals were filtered off, washed with water and dried. Whereby 2.2 g of crystals were obtained. 1.85 g of the crystals were obtained by recrystallizing with ethanol. Melting point is 147° to 149° C.

Elementary analysis for ($C_{29}H_{30}N_4O$)

Calculated (%) C:77.30 H:6.71 N:12.43

Found (%) C:77.46 H:6.89 N:12.24

EXAMPLE 5

4-(4-methoxyphenyl)-2-methyl-6-(2-piperidinoethoxy)pyrimidine dihydrochloride 1.17 g of 4-chloro-6-(4-methoxyphenyl)-2-methylpyrimidine and 0.65 g of 2-piperidinoethanol were dissolved in 10 ml of dried tetrahydrofuran. After the addition of 60% sodium hydride 0.2 g, the mixture was stirred for 3 hours at room temperature. The reaction mixture was poured into ice-water, and then was extracted with ethyl acetate. The extract was washed with water and was dried with anhydrous magnesium sulfate, and then this was evaporated in vacuo. The residue was purified with column chromatography with silica gel(Wako gel c-200 150 g, elution with chloroform and then chloroform: methanol=99:1), resulting 1.3 g of oily substance. This was dissolved in 10 ml of ethanol, 3 ml of 20% ethanol hydrochloride was added and evaporated in vacuo. Ether was added to the residue to crystallize. Whereby 1.32 g of crystals were obtained. These were recrystallized with isopropanol, resulting to obtain 0.83 g of crystals. Melting point is 165° to 167° C.

Elementary analysis for $(C_{19}H_{25}N_2O \cdot 2HCl)$
Calculated (%) C:57.00 H:6.80 N:10.50
Found (%) C:57.28 H:6.94 N:10.31

In the same way as mentioned in practice example to 5, the following compounds were prepared.

EXAMPLE 6

4-[2-(N,N-diethylamino)ethoxy]-6-methyl-2-phenylpyrimidine dihydrochloride

Melting point 150°–153° C.
Elementary analysis for $(C_{17}H_{23}N_3O_2 \cdot 2HCl)$
Calculated (%) C:56.99 H:7.03 N:11.73
Found (%) C:56.73 H:6.98 N:11.67

EXAMPLE 7

4-[2-(N,N-dimethylamino)ethoxy]-6-methyl-2-phenylpyrimidine dihydrochloride

Melting point 184°–186° C.
Elementary analysis for $(C_{15}H_{19}N_3O \cdot 2HCl)$
Calculated (%) C:54.55 H:6.41 N:12.72
Found (%) C:54.31 H:6.78 N:12.56

EXAMPLE 8

4-Methyl-2-phenyl-6-(2-piperidinoethoxy) pyrimidine dihydrochloride

Melting point 179°–181° C.
Elementary analysis for $(C_{18}H_{23}N_3O \cdot 2HCl)$
Calculated (%) C:58.38 H:6.80 N:11.35
Found (%) C:58.13 H:6.96 N:11.14

EXAMPLE 9

4-Methyl-2-phenyl-6-(2-morpholinoethoxy) pyrimidine dihydrochloride

Melting point 181°–182° C.
Elementary analysis for $(C_{17}H_{21}N_3O_2 \cdot 2HCl)$
Calculated (%) C:54.85 H:6.23 N:11.29
Found (%) C:54.61 H:6.48 N:11.46

EXAMPLE 10

4-Methyl-2-phenyl-6-(3-piperidinopropoxy) pyrimidine dihydrochloride

Melting point 175°–177° C.
Elementary analysis for $(C_{19}H_{25}N_3O \cdot 2HCl)$
Calculated (%) C:59.38 H:7.08 N:10.98
Found (%) C:59.29 H:7.23 N:10.97

EXAMPLE 11

4-Methyl-2-phenyl-6-[2-(4-phenylpiperazino)ethoxy] pyrimidine maleate

Melting point 172°–173° C.
Elementary analysis for $(C_{23}H_{26}N_4O \cdot C_4H_4O_4)$
Calculated (%) C:66.11 H:6.16 N:11.42
Found (%) C:66.33 H:6.01 N:11.53

EXAMPLE 12

4-[2-[4-(4-methoxyphenyl)piperazino]ethoxy]-6-methyl-2-phenylpyrimidine maleate

Melting point 128°–129° C.
Elementary analysis for $(C_{24}H_{28}N_4O_2 \cdot C_4H_4O_4)$
Calculated (%) C:64.60 H:6.20 N:10.76
Found (%) C:64.70 H:6.19 N:10.75

EXAMPLE 13

4-[2-(4-diphenylmethylpiperazino)ethoxy]-6-methyl-2-phenylpyrimidine

Melting point 113°–115° C.
Elementary analysis for $(C_{30}H_{32}N_4O)$
Calculated (%) C:77.56 H:6.94 N:12.06
Found (%) C:77.69 H:7.14 N:12.00

EXAMPLE 14

4-[3-(4-diphenylmethylpiperazino)propoxy]-6-methyl-2-phenylpyrimidine dimaleate

Melting point 174°–175° C.
Elementary analysis for $(C_{31}H_{34}N_4O \cdot 2C_4H_4O_4)$
Calculated (%) C:65.90 H:5.95 N:7.88
Found (%) C:66.09 H:6.18 N:8.09

EXAMPLE 15

4-(1-azabicyclo[2,2,2]octo-3-yloxy)-6-methyl-2-phenylpyrimidine maleate

Melting point 176°–177° C.
Elementary analysis for $(C_{18}H_{21}N_3O \cdot C_4H_4O_4)$
Calculated (%) C:64.22 H:6.12 N:10.21
Found (%) C:64.36 H:6.17 N:10.08

EXAMPLE 16

4-[2-(N,N-diethylamino)ethoxy]-2-(4-methoxyphenyl)-6-methylpyrimidine dihydrochloride Melting point 182°–184° C.
Elementary analysis for $(C_{18}H_{25}N_3O_2 \cdot 2HCl)$
Calculated (%) C:55.67 H:7.01 N:10.82
Found (%) C:55.83 H:7.04 N:10.90

EXAMPLE 17

4-[2-(N,N-dimethylamino)ethoxy]-
2-(4-methoxyphenyl)-6-methylpyrimidine
dihydrochloride Melting point 197°–198° C.
Elementary analysis for ($C_{16}H_{21}N_3O_2 \cdot 2HCl$)
Calculated (%) C:53.34 H:6.43 N:11.66
Found (%) C:53.57 H:6.78 N:11.64

EXAMPLE 18

2-(4-methoxyphenyl)-4-methyl-
6-(2-piperidinoethoxy)pyrimidine dihydrochloride

Melting point 179°–181° C.
Elementary analysis for ($C_{19}H_{25}N_3O_2 \cdot 2HCl$)
Calculated C:57.00 H:6.80 N:10.50
Found (%) C:56.90 H:6.99 N:10.37

EXAMPLE 19

2-(4-methoxyphenyl)-4-methyl-
6-(2-morpholinoethoxy)pyrimidine dihydrochloride

Melting point 206°–209° C.
Elementary analysis for ($C_{18}H_{23}N_3O_3 \cdot 2HCl$)
Calculated (%) C:53.74 H:6.26 N:10.44
Found (%) C:53.72 H:6.41 N:10.47

EXAMPLE 20

2-(4-methoxyphenyl)-4-methyl-
6-(3-piperidinopropoxy)pyrimidine dihydrochloride

Melting point 187°–188° C.
Elementary analysis for ($C_{20}H_{27}N_3O_2 \cdot 2HCl$)
Calculated (%) C:57.97 H:7.05 N:10.14
Found (%) C:57.88 H:7.19 N:10.08

EXAMPLE 21

2-(4-methoxyphenyl)-4-methyl-
6-[2-(4-phenylpiperazino) ethoxy]pyrimidine

Melting point 83°–85° C.
Elementary analysis for ($C_{24}H_{26}N_4O_2$)
Calculated (%) C:71.26 H:6.98 N:13.85
Found (%) C:71.22 H:7.11 N:13.77

EXAMPLE 22

2-(4-methoxyphenyl)-
4-[2-[4-(4-methoxyphenyl)piperazino]ethoxy]
6-methylpyrimidine maleate Melting point 149°–150° C.

Elementary analysis for ($C_{25}H_{30}N_4O_3 \cdot C_4H_4O_4$)

Calculated (%) C:63.26 H:6.22 N:10.18
Found (%) C:63.36 H:6.17 N:10.15

EXAMPLE 23

2-(4-methoxyphenyl)-4-methyl-
6-[2-(4-phenylpiperidino) ethoxy]pyrimidine
dihydrochloride Melting point 151°–155° C.
Elementary analysis for ($C_{25}H_{29}N_3O_2 \cdot 2HCl$)
Calculated (%) C:63.02 H:6.56 N:8.82
Found (%) C:62.86 H:6.37 N:8.98

EXAMPLE 24

4-[2-[4-(4-chlorobenzoyl)piperazino]ethoxy]-
2-(4-methoxyphenyl) 6-methylpyrimidine maleate Melting point 164°–165° C.
Elementary analysis for ($C_{25}H_{27}ClN_4O_2 \cdot C_4H_4O_4$)
Calculated (%) C:59.74 H:5.36 N:9.61
Found (%) C:59.40 H:5.46 N:9.59

EXAMPLE 25

4-[2-[4-(4-methoxybenzoyl)piperazino]ethoxy]-
2-(4-methoxyphenyl) 6-methylpyrimidine maleate Melting point 156°–157° C.
Elementary analysis for ($C_{26}H_{30}N_4O_4 \cdot C_4H_4O_4$)
Calculated (%) C:62.27 H:5.92 N:9.68
Found (%) C:62.11 H:6.14 N:9.67

EXAMPLE 26

4-(1-azabicyclo[2,2,2]octo-3-yloxy)-
2-(4-fluorophenyl)-6-methylpyrimidine maleate Melting point 141.5°–143° C.
Elementary analysis for ($C_{18}H_{20}FN_3O \cdot C_4H_4O_4$)
Calculated (%) C:61.52 H:5.63 N:9.78
Found (%) C:61.74 H:5.92 N:9.71

EXAMPLE 27

(R)-(–)-4-(1-azabicyclo[2,2,2]octo-3-yloxy)-
2-(4-fluorophenyl) 6-methylpyrimidine maleate Melting point 155.5°–156.5° C.
Elementary analysis for ($C_{18}H_{20}FN_3O \cdot C_4H_4O_4$)
Calculated (%) C:61.52 H:5.63 N:9.78
Found (%) C:61.30 H:5.92 N:9.81
Specific rotation $[\alpha]_D$ (20° C.)=–18.69 (c=1, $H_2O$)

(R)-(–)-4-(1-azabicyclo[2,2,2]octo-3-yloxy)-
2-(4-fluorophenyl) 6-methylpyrimidine
hydrochloride Melting point 277°–278° C.
Elementary analysis for ($C_{18}H_{20}FN_3O \cdot HCl$)
Calculated (%) C:61.80 H:6.05 N:12.01
Found (%) C:61.57 H:5.95 N:12.08
Specific rotation $[\alpha]_D$ (20° C.)=–24.77 (c=1, $H_2O$)

EXAMPLE 28

(S)-(+)-4-(1-azabicyclo[2,2,2]octo-3-yloxy)-
2-(4-methoxyphenyl) 6-methylpyrimidine maleate Melting point 159°–161° C.
Elementary analysis for ($C_{19}H_{23}N_3O_2 \cdot C_4H_4O_4$)
Calculated (%) C:62.57 H:6.16 N:9.52
Found (%) C:62.30 H:6.34 N:9.71
Specific rotation $[\alpha]_D$ (20° C.)=+32.5 (c=1, $H_2O$)

EXAMPLE 29

4-(1-azabicyclo[2,2,2]octo-3-yloxy)-
2-(4-chlorophenyl)-6-methylpyrimidine maleate Melting point 161°–162°–C.
Elementary analysis for ($C_{18}H_{20}ClN_3O \cdot C_4H_4O_4$)
Calculated (%) C:59.26 H:5.43 N:9.42
Found (%) C:59.30 H:5.38 N:9.37

EXAMPLE 30

4-methylamino-6-methyl-2-phenylpyrimidine

Melting point 69°–71° C.
Elementary analysis for ($C_{12}H_{13}N_3$)
Calculated (%) C:72.33 H:6.57 N:21.09
Found (%) C:72.36 H:6.69 N:21.14

EXAMPLE 31

4-(N,N-diethylamino)-6-methyl-2-phenylpyrimidine
hydrochloride

Melting point 161°–163° C.
Elementary analysis for ($C_{15}H_{19}N_3 \cdot HCl$)
Calculated (%) C:64.85 H:7.26 N:15.13
Found (%) C:64.69 H:7.43 N:15.37

EXAMPLE 32

4-methyl-6-(2-morpholinoethylamino)-
2-phenylpyrimdine dihydrochloride

Melting point 251°–253.5° C.
Elementary analysis for ($C_{17}H_{22}N_4O \cdot 2HCl$)
Calculated (%) C:54.99 H:6.51 N:15.09
Found (%) C:55.14 H:6.38 N:15.38

EXAMPLE 33

4-[2-(N,N-diisopropylamino)ethylamino]-
6-methyl-2-phenylpyrimidine dihydrochloride Melting point 255°–256° C.
Elementary analysis for ($C_{19}H_{28}N_4 \cdot 2HCl$)
Calculated (%) C:59.21 H:7.84 N:14.54
Found (%) C:59.43 H:7.66 N:14.68

EXAMPLE 34

4-methyl-6-(4-phenylpiperazino)-2-phenylpyrimidine

Melting point 95°–97° C.
Elementary analysis for ($C_{21}H_{22}N_4$)
Calculated (%) C:76.33 H:6.71 N:16.95
Found (%) C:76.16 H:6.82 N:16.69

EXAMPLE 35

4-(4-diphenylmethylpiperazino)-6-methyl-
2-phenylpyrimidine

Melting point 201°–203° C.
Elementary analysis for ($C_{28}H_{28}N_4$)
Calculated (%) C:79.97 H:6.71 N:13.32
Found (%) C:79.99 H:6.88 N:13.12

EXAMPLE 36

4-amino-2-(4-methoxyphenyl)-6-methylpyrimidine

Melting point 177°–180° C.
Elementary analysis for ($C_{12}H_{13}N_3O$)
Calculated (%) C:66.96 H:6.09 N:19.52
Found (%) C:67.09 H:6.20 N:19.42

EXAMPLE 37

2-(4-methoxyphenyl)-4-methyl-
6-methylaminopyrimidine

Melting point 99°–101° C.
Elementary analysis for ($C_{13}H_{15}N_3O$)
Calculated (%) C:68.10 H:6.59 N:18.33
Found (%) C:68.50 H:6.76 N:18.41

EXAMPLE 38

2-(4-methoxyphenyl)-4-methyl-
6-(2-morpholinoethylamino) pyrimidine

Melting point 144°–146° C.
Elementary analysis for ($C_{18}H_{24}N_4O_2$)
Calculated (%) C:65.83 H:7.37 N:17.06
Found (%) C:65.69 H:7.45 N:16.82

EXAMPLE 39

4-[2-(N,N-diethylamino)ethoxy]-
2-methyl-6-phenylpyrimidine dihydrochloride

Melting point 195°–197° C.
Elementary analysis for ($C_{17}H_{23}N_2O \cdot 2HCl$)
Calculated (%) C:56.99 H:7.03 N:11.73
Found (%) C:56.90 H:7.19 N:11.75

EXAMPLE 40

4-[2-(4-diphenylmethylpiperazino)ethoxy]-2-methyl
-6-phenylpyrimidine

Melting point 129°–130° C.
Elementary analysis for ($C_{30}H_{32}N_4O$)
Calculated (%) C:77.56 H:6.94 N:12.06
Found (%) C:77.38 H:7.15 N:11.92

EXAMPLE 41

4-[2-(N,N-diethylamino)ethoxy]-
6-(4-methoxyphenyl)-2-methylpyrimidine
dihydrochloride Melting point 168°–171° C.
Elementary analysis for ($C_{18}H_{25}N_3O_2 \cdot 2HCl$)
Calculated (%) C:55.67 H:7.01 N:10.82
Found (%) C:55.49 H:6.83 N:10.98

EXAMPLE 42

4-[2-(4-diphenylmethylpiperazino)ethoxy]-
6-(4-methoxyphenyl)-2-methylpyrimidine Melting point 131°–133° C.
Elementary analysis for ($C_{31}H_{34}N_4O_2$)
Calculated (%) C:75.28 H:6.93 N:11.33
Found (%) C:74.77 H:7.00 N:11.24

EXAMPLE 43

4-(1-azabicyclo[2,2,2]octo-3-yloxy)-
6-(4-methoxyphenyl)-2-methylpyrimidine maleate Melting point 145°–147° C.
Elementary analysis for ($C_{19}H_{23}N_3O_2 \cdot C_4H_4O_4$)
Calculated (%) C:62.57 H:6.16 N:9.52
Found (%) C:62.30 H:6.34 N:9.62

EXAMPLE 44

(R)- (–)-4-(1-azabicyclo[2,2,2]octo-
3-yloxy)-2-(4-chlorophenyl) 6-methylpyrimidine
maleate Melting point 166°–167° C.
Elementary analysis for ($C_{18}H_{20}ClN_3O \cdot C_4H_4O_4$)
Calculated (%) C:59.26 H:5.43 N:9.42
Found (%) C:59.10 H:5.34 N:9.61
Specific rotation $[\alpha]_D$ (20° C.)=–35.03 (c=1, $H_2O$)

EXAMPLE 45

2-methyl-4-(2-morpholinoethylamino)-
6-phenylpyrimidine dihydrochloride

Melting point 277°–282° C.
Elementary analysis for ($C_{17}H_{22}N_4O$)
Calculated (%) C:54.99 H:6.51 N:15.09
Found (%) C:54.81 H:6.63 N:14.90

EXAMPLE 46

4-(4-diphenylmethylpiperazino)-
2-methyl-6-phenylpyrimidine

Melting point 195°–198° C.
Elementary analysis for ($C_{28}H_{28}N_4$)
Calculated (%) C:79.96 H:6.71 N:13.32
Found (%) C:79.73 H:6.89 N:13.23

EXAMPLE 47

(R)-(–)-4-(1-azabicyclo[2,2,2]octo-3-yloxy)-
2-(4-chlorophenyl) 6-methylpyrimidine
hydrochloride Melting point 284°–285.5° C.
Elementary analysis for ($C_{18}H_{20}ClN_3O \cdot HCl$)
Calculated (%) C:59.02 H:5.78 N:11.47
Found (%) C:58.79 H:5.66 N:11.51
Specific rotation $[\alpha]_D$ (20° C.)=–21.47 (c=1, $H_2O$)

EXAMPLE 48

4-(1-azabicyclo[2,2,2]octo-3-yloxy)-
2-(4-methoxyphenyl)-6-trifluoromethylpyrimidine
maleate Melting point 173°–174.5° C.
Elementary analysis for ($C_{23}H_{24}F_3N_3O_6$)
Calculated (%) C:55.76 H:4.88 N:8.48
Found (%) C:55.83 H:5.07 N:8.55

EXAMPLE 49

4-(1-azabicyclo[2,2,2]octo-3-yloxy)-
6-methyl-2-(4-trifluoromethylphenyl) pyrimidine
maleate Melting point 173.5°–174.5° C.
Elementary analysis for ($C_{23}H_{24}F_3N_3O_5$)
Calculated (%) C:57.62 H:5.05 N:8.76
Found (%) C:58.00 H:5.14 N:8.90

EXAMPLE 50

4-(1-azabicyclo[2,2,2]octo-3-yloxy)-
2-(4-trifluoromethylphenyl)
6-trifluoromethylpyrimidine maleate Melting point 171°–172° C.
Elementary analysis for ($C_{19}H_{17}F_6N_3O \cdot C_4H_4O_4$)
Calculated (%) C:51.79 H:3.97 N:7.88
Found (%) C:51.88 H:4.03 N:7.93

EXAMPLE 51

4-(1-azabicyclo[2,2,2]octo-3-yloxy)-
2-(4-fluorophenyl)-6-trifluoromethylpyrimidine
maleate Melting point 176°–177.5° C.
Elementary analysis for ($C_{19}H_{17}F_4N_2O \cdot C_4H_4O_4$)
Calculated (%) C:54.66 H:4.38 N:8.69
Found (%) C:54.44 H:4.42 N:8.76

EXAMPLE 52

4-[2-(4-diphenylmethylpiperazino)ethoxy]-
2-(4-fluorophenyl)-6-methylpyrimidine

Melting point 120°–121.5° C.
Elementary analysis for ($C_{30}H_{31}FN_4O$)
Calculated (%) C:74.66 H:6.47 N:11.61
Found (%) C:74.58 H:6.62 N:11.51

EXAMPLE 53

4-[2-[4-[bis(4-fluorophenyl)methyl]
piperazino]ethoxy]-2-(4-methoxyphenyl)
6-methylpyrimidine Melting point 125°–126° C.
Elementary analysis for ($C_{31}H_{32}F_2N_4O_2$)
Calculated (%) C:70.17 H:6.08 N:10.56
Found (%) C:70.11 H:6.06 N:10.55

EXAMPLE 54

4-[2-(4-diphenylmethylpiperazino)ethoxy]-
6-methyl-2-(4-trifluoromethylphenyl)pyrimidine Melting point 161.5°–162.5° C.
Elementary analysis for ($C_{31}H_{31}F_3N_4O$)
Calculated (%) C:69.91 H:5.87 N:10.52
Found (%) C:69.51 H:5.82 N:10.51

EXAMPLE 55

4-[2-[4-[bis(4-fluorophenyl)methyl]
piperazino]ethoxy]-6-methyl
2-(4-trifluoromethylphenyl)pyrimidine Melting point 104.5°–106° C.
Elementary analysis for ($C_{31}H_{29}F_5N_4O$)
Calculated (%) C:65.49 H:5.14 N:9.85
Found (%) C:65.53 H:5.16 N:9.79

EXAMPLE 56

4-[2-(4-diphenylmethylpiperazino)ethoxy]-
2-(4-methoxyphenyl) 6-trifluoromethylpyrimidine Melting point 117°–118° C.
Elementary analysis for ($C_{31}H_{31}F_3N_4O_2$)
Calculated (%) C:67.87 H:5.70 N:10.21
Found (%) C:67.51 H:5.65 N:10.29

EXAMPLE 57

4-[2-[4-[bis(4,-fluorophenyl)methyl]
piperazino]ethoxy]-2-(4-methoxyphenyl)
6-trifluoromethylpyrimidine Melting point 104°–106° C.
Elementary analysis for ($C_{31}H_{29}F_5N_4O_2$)
Calculated (%) C:63.69 H:5.00 N:9.58
Found (%) C:63.31 H:5.15 N:9.36

EXAMPLE 58

(R)-(−)-4-(1-azabicyclo[2,2,2]octo-3-yloxy)-
2-(4-hydroxyphenyl) 6-methylpyrimidine maleate Melting point 177°–179° C.
Elementary analysis for ($C_{18}H_{21}N_3O_2 \cdot C_4H_4O_4$)
Calculated (%) C:61.82 H:5.89 N:9.83
Found (%) C:61.50 H:5.90 N:9.82
Specific rotation $[\alpha]_D$ (20° C.)=−35.77 (c=1, $H_2O$)

EXAMPLE 59

4-(1-azabicyclo[2,2,2]octo-3-yloxy)-6-tert-butyl-
2-(4-methoxyphenyl)pyrimidine maleate Melting point 198°–199° C.
Elementary analysis for ($C_{22}H_{29}N_3O_2 \cdot C_4H_4O_4$)
Calculated (%) C:64.58 H:6.88 N:8.69
Found (%) C:64.77 H:6.81 N:8.73

EXAMPLE 60

(R)-(−)-4-(1-azabicyclo[2,2,2]octo-3-yloxy)-
6-tert-butyl-2-(4-methoxyphenyl)pyrimidine maleate Melting point 203°–204° C.
Elementary analysis for ($C_{22}H_{29}N_3O_2 \cdot C_4H_4O_4$)

Calculated (%) C:64.58 H:6.88 N:8.69

Found (%) C:64.61 H:6.93 N:8.63

Specific rotation $[\alpha]_D$ (20° C.)=−41.26 (c=1, $CH_3OH$)

EXAMPLE 61

4-(1-azabicyclo[2,2,2]octo-3-yloxy)-6-tert-butyl-
2-(4-fluorophenyl)pyrimidine maleate Melting point 186°–187° C.
Elementary analysis for ($C_{21}H_{26}FN_3O_2 \cdot C_4H_4O_4$)
Calculated (%) C:63.68 H:6.41 N:8.91
Found (%) C:63.68 H:6.42 N:8.85

EXAMPLE 62

(R)-(−)-4-(1-azabicyclo[2,2,2]octo-3-yloxy)-
6-tert-butyl-2-(4-fluorophenyl)pyrimidine maleate Melting point 203°–205° C.
Elementary analysis for ($C_{21}H_{26}FN_3O_2 \cdot C_4H_4O_4$)
Calculated (%) C:63.68 H:6.41 N:8.91
Found (%) C:63.62 H:6.42 N:8.87
Specific rotation $[\alpha]_D$ (20° C.)=−30.63 (c=1, $CH_3OH$)

EXAMPLE 63

(R)-(−)-4-(1-azabicyclo[2,2,2]octo-3-yloxy)-
2-(4-fluorophenyl) 6-trifluoromethylpyrimidine
maleate Melting point 172°–173.5° C.
Elementary analysis for ($C_{18}H_{17}F_4N_3O \cdot C_4H_4O_4$)
Calculated (%) C:54.66 H:4.38 N:8.69
Found (%) C:54.43 H:4.38 N:8.78
Specific rotation $[\alpha]_D$ (20° C.)=−41.54 (c=1, $CH_3OH$)

EXAMPLE 64

4-[2-[4-bis(4-fluorophenyl)methyl]piperazino]
ethoxy]-2-(4-fluorophenyl) 6-methylpyrimidine
trihydrochloride Melting point 176°–177° C.
Elementary analysis for ($C_{30}H_{29}F_3N_4O \cdot 3HCl$)
Calculated (%) C:57.38 H:5.14 N:8.92
Found (%) C:57.16 H:5.38 N:8.73

Test Examples

Results of pharmacological tests showing the usefulness of representative compounds of the present invention are given.

Methods (1) Improvement effects on deficits of learning and memory induced by scopolamine.

A test drug suspended in 0.5% methyl cellulose (MC) solution was administered orally to ten rats in a group. 30 minutes after this treatment, scopolamine at a dose of 0.3 mg/kg was given intraperitoneally to the animals. 30 minutes after the treatment of scopolamine, training trials of the step-through type passive avoidance task were carried out. 24 hours after the trial, test trials were carried out.

The step-through latency time in the test trial of rats was measured for up to 300 sec. The results were regarded as learning scores. (Table 1). The statistical significance compared with the control groups was analyzed using Kruskal-Wallis's test and Fisher's test. MC solution was given to the control groups.

TABLE 1

Improving effects on deficits of learning and memory (rats)

| Drugs (Example NO.) | Dose p.o. | Latency (sec.) |
|---|---|---|
| 1 | 0.03 | 170.80±44.15 |
|  | 0.1 | 228.20±37.47** |
|  | 0.3 | 247.30±35.16** |
|  | 1 | 242.90±38.07** |
|  | 3 | 255.30±30.85** |
|  | 10 | 253.50±31.18** |
|  | 30 | 182.40±40.25 |
| MC | — | 98.30±43.95 |
| 2 | 0.01 | 161.30±46.33 |
|  | 0.03 | 231.40±35.92* |
|  | 0.1 | 253.10±31.62** |
|  | 0.3 | 271.00±29.00** |
|  | 1 | 245.40±36.48** |
|  | 3 | 249.60±33.86** |
|  | 10 | 192.60±43.89 |
| MC | — | 90.20±35.71 |
| 3 | 0.3 | 191.50±44.37 |
|  | 1 | 239.90±31.58* |
|  | 3 | 244.20±37.21** |
|  | 10 | 276.70±23.30** |
|  | 30 | 272.10±27.90** |
| MC | — | 109.40±41.87 |
| 4 | 1 | 143.90±43.53 |
|  | 3 | 204.50±40.47 |
|  | 10 | 245.70±36.29** |
|  | 30 | 279.20±20.80** |
| MC | — | 106.80±42.66 |
| 6 | 0.1 | 179.80±36.66 |
|  | 0.3 | 200.40±41.39* |
|  | 1 | 222.80±40.06* |
|  | 3 | 223.50±39.45* |
|  | 10 | 188.10±40.24 |
| MC | — | 99.90±43.83 |
| 10 | 1 | 212.70±44.45 |
|  | 3 | 274.00±26.00** |
|  | 10 | 248.40±34.40** |
|  | 30 | 222.40±39.90* |
|  | 100 | 208.50±38.37 |
| MC | — | 133.00±43.62 |
| 13 | 0.3 | 131.10±46.13 |
|  | 1 | 186.10±46.51 |
|  | 3 | 286.50±13.50** |
|  | 10 | 245.70±36.20** |
|  | 30 | 242.60±38.27* |

TABLE 1-continued

Improving effects on deficits of learning and memory (rats)

| Drugs (Example NO.) | Dose p.o. | Latency (sec.) |
|---|---|---|
|  | 100 | 169.20±44.09 |
| MC | — | 105.50±42.59 |
| 15 | 1 | 270.50±29.50* |
| MC | — | 129.00±46.60 |
| 21 | 1 | 170.00±44.05 |
|  | 3 | 243.50±37.67* |
|  | 10 | 272.70±27.30** |
|  | 30 | 276.90±23.10** |
| MC | — | 132.00±45.90 |
| 23 | 0.3 | 156.40±47.90 |
|  | 1 | 243.10±37.93* |
|  | 3 | 270.90±29.10** |
|  | 10 | 274.00±26.00** |
|  | 30 | 272.00±28.00** |
| MC | — | 104.40±42.79 |
| 26 | 0.03 | 217.80±41.86 |
|  | 0.1 | 249.30±33.84* |
|  | 0.3 | 271.00±29.00** |
|  | 1 | 274.50±25.50** |
|  | 3 | 273.10±26.90** |
|  | 10 | 271.50±28.50** |
|  | 30 | 185.70±46.69** |
| MC | — | 135.50±44.95 |
| 27 | 0.01 | 214.90±43.34 |
|  | 0.03 | 247.80±34.80* |
|  | 0.1 | 272.90±27.10** |
|  | 0.3 | 271.60±28.40** |
|  | 1 | 274.00±26.00** |
|  | 3 | 272.90±27.10** |
|  | 10 | 167.70±44.20 |
| MC | — | 133.80±45.31 |
| 35 | 0.1 | 153.10±41.22 |
|  | 0.3 | 162.40±40.34 |
|  | 1 | 253.30±31.14 |
|  | 3 | 274.90±25.10 |
|  | 10 | 173.20±42.51 |
| MC | — | 166.80±44.59 |
| 44 | 0.03 | 196.80±42.16 |
|  | 0.1 | 272.00±28.00** |
|  | 0.3 | 271.40±28.60** |
|  | 1 | 273.30±26.70** |
|  | 3 | 271.00±29.00** |
|  | 10 | 246.60±35.63* |
|  | 30 | 196.70±42.51 |
| MC | — | 129.80±46.35 |
| 58 | 0.01 | 215.90±42.89 |
|  | 0.03 | 252.00±32.42* |
|  | 0.1 | 274.20±25.80** |
|  | 0.3 | 272.50±27.50** |
|  | 1 | 272.80±27.20** |
|  | 3 | 187.10±46.11 |
| MC | — | 132.10±45.74 |

MC: 0.5% methyl cellulose
*p<0.05
**P<0.01

(2) Binding affinities for muscarinic receptors

The binding assay for muscarinic receptors was carried out according to the method of Yamamura and Snyder [Yamamura, H. I. and Snyder, S. H.; Muscarinic cholinergic binding in rat brain. Proc.Natl.Acad. Sci. U.S.A.71:1725–1729 (1974)]. Namely the receptor membrane preparations from rat brain were incubated with 0.1 nM [$^3$H]quinuclidinyl benzilate (QNB) in mM Na/K phosphate buffer solution (pH 7.4) at 25° C. for 60 minutes. The strength of the binding affinity for muscarinic receptors was indicated as the concentration of drug required to displace 50% of the [$^3$H]QNB binding ($IC_{50}$). The results are shown in Table 2.

TABLE 2

Binding affinities for muscarinic receptors

| Drugs (Example NO.) | IC$_{50}$ (M) |
|---|---|
| 1 | $7.8 \pm 10^{-6}$ |
| 2 | $3.5 \pm 10^{-6}$ |
| 15 | $3.3 \pm 10^{-6}$ |
| 26 | $2.9 \pm 10^{-6}$ |
| 27 | $1.6 \pm 10^{-6}$ |
| 29 | $1.6 \pm 10^{-6}$ |
| 44 | $1.4 \pm 10^{-6}$ |
| 51 | $2.7 \pm 10^{-6}$ |
| 58 | $9.9 \pm 10^{-5}$ |
| 59 | $7.2 \pm 10^{-6}$ |
| 61 | $5.8 \pm 10^{-6}$ |
| 62 | $7.4 \pm 10^{-6}$ |
| 63 | $3.7 \pm 10^{-6}$ |
| carbachol | $1.0 \pm 10^{-4}$ |
| pilocarpine | $8.3 \pm 10^{-6}$ |

The compounds of the present invention exhibited equivalent or superior binding affinities for the central muscarinic receptors compared with pilocarpine or carbachol.

(3) Effect on muscarinic $M_1$ receptors

Binding assay for muscarinic $M_1$ receptors was carried out according to the method of Watson and Yamamura [Life Sci. 3001–3011(1983)]. Namely, the receptor membrane preparations from rat brain were incubated with 1 nM [$^3$H]pirenzepine in 10 mM Na/K phosphate buffer solution (pH 7.4) at 25° C. for 60 minutes. 1 µM of atropine was used as a displacer. The degree of binding affinities for muscarinic $M_1$ receptors were shown in table 3 as the concentration of drug which was required to displace 50% of the [$^3$H] pirenzedine binding (IC$_{50}$).

TABLE 3

Effects on muscarinic $M_1$ receptors

| Drugs (Example NO.) | IC$_{50}$ (M) |
|---|---|
| 2 | $6.5 \pm 10^{-7}$ |
| 27 | $1.7 \pm 10^{-7}$ |
| 44 | $2.4 \pm 10^{-7}$ |
| 58 | $8.1 \pm 10^{-7}$ |
| 60 | $3.1 \pm 10^{-6}$ |
| 62 | $2.8 \pm 10^{-6}$ |
| 63 | $6.0 \pm 10^{-7}$ |
| carbachol | $1.2 \pm 10^{-5}$ |

As shown in table 3, the compounds of the present invention exhibited inhibitory effects on the binding of [$^3$H]pirenzepine to $M_1$ receptors. These effects were 10 to 100 times more potent than that of carbachol.

(4) Acute toxicity

Male mice, 6 weeks of age (4 mice/group) were deprived of foods overnight. Test drugs suspended in 0.5% methyl cellulose solution were administered orally to the mice. Whether the animals were dead or not was observed 72 hours after the treatment of the drugs. The results were shown in table 4.

TABLE 4

Acute toxicity (mice, p.o.)

| Drugs (Example NO.) | Dose (mg/kg) | Lethality |
|---|---|---|
| 3 | 1000 | 0/4 |
| 4 | 1000 | 0/4 |
| 11 | 1000 | 0/4 |
| 13 | 1000 | 0/4 |
| 21 | 1000 | 0/4 |
| 35 | 1000 | 0/4 |
| 44 | 1000 | 0/4 |
| 58 | 1000 | 0/4 |

(Number of dead animals/Number of animals used)

It is clear from the table 4 that no death was observed when all of the compounds of the present invention administered to the animals at a dose of 1000 mg/kg. Pharmaceutical examples Pharmaceutical preparations using the compounds of the present invention are as follows.

Pharmaceutical example 1 Injection

The injection in which the following prescription contained in 1 ml of an ampule was prepared according to the usual method.

| Prescription | The compound of Example 2 | 1 mg |
|---|---|---|
| | sodium chloride | 9 mg |
| | water for injection | q.s. |

Pharmaceutical example 2 Injection

The injection in which the following prescription contained in 1 ml of an ampule was prepared according to the usual method.

| Prescription | The compound of Example 27 | 1 mg |
|---|---|---|
| | sodium chloride | 9 mg |
| | water for injection | q.s. |

Pharmaceutical example 3 Injection

The injection in which the following prescription contained in 1 ml of an ampule was prepared according to the usual method.

| Prescription | The compound of Example 44 | 1 mg |
|---|---|---|
| | sodium chloride | 9 mg |
| | water for injection | q.s. |

Pharmaceutical example 4 Injection

The injection in which the following prescription contained in 1 ml of an ampule was prepared according to the usual method.

| Prescription | The compound of Example 58 | 1 mg |
|---|---|---|
| | sodium chloride | 9 mg |
| | water for injection | q.s. |

Pharmaceutical example 5 Oral liquid preparation

The oral liquid in which the following prescription contained in 100 ml was prepared according to the usual method.

| Prescription | The compound of Example 2 | 20 mg |
|---|---|---|
| | simple syrup | q.s. |

Pharmaceutical example 6 Oral liquid preparation

The oral liquid in which the following prescription contained in 100 ml was prepared according to the usual method.

| Prescription | The compound of Example 27 | 20 mg |
|---|---|---|
| | simple syrup | q.s. |

Pharmaceutical example 7 Oral liquid preparation

The oral liquid in which the following prescription contained in 100 ml was prepared according to the usual method.

| Prescription | The compound of Example 44 | 20 mg |
|---|---|---|
| | simple syrup | q.s. |

Pharmaceutical example 8 oral liquid preparation

The oral liquid in which the following prescription contained in 100 ml was prepared according to the usual method.

| Prescription | The compound of Example 58 | 20 mg |
|---|---|---|
| | simple syrup | q.s. |

Pharmaceutical example 9 Solid formulation

The tablet in which the following prescription contained in 120 mg of one tablet was prepared according to the usual method.

| Prescription | The compound of Example 2 | 1 mg |
|---|---|---|
| | lactose | 60 mg |
| | cornstarch | 30 mg |
| | crystalline cellulose | 20 mg |
| | hydroxypropylcellulose | 7 mg |
| | magnesium stearate | 2 mg |

Pharmaceutical example 10 Solid formulation

The tablet in which the following prescription contained in 120 mg of one tablet was prepared according to the usual method.

| Prescription | The compound of Example 27 | 1 mg |
|---|---|---|
| | lactose | 60 mg |
| | cornstarch | 30 mg |
| | crystalline cellulose | 20 mg |
| | hydroxypropylcellulose | 7 mg |
| | magnesium stearate | 2 mg |

Pharmaceutical example 11 Solid formulation

The tablet in which the following prescription contained in 120 mg of one tablet was prepared according to the usual method.

| Prescription | The compound of Example 44 | 1 mg |
|---|---|---|
| | lactose | 60 mg |
| | cornstarch | 30 mg |
| | crystalline cellulose | 20 mg |
| | hydroxypropylcellulose | 7 mg |
| | magnesium stearate | 2 mg |

Pharmaceutical example 12 Solid formulation

The tablet in which the following prescription contained in 120 mg of one tablet was prepared according to the usual method.

| Prescription | The compound of Example 58 | 1 mg |
|---|---|---|
| | lactose | 60 mg |
| | cornstarch | 30 mg |
| | crystalline cellulose | 20 mg |
| | hydroxypropylcellulose | 7 mg |
| | magnesium stearate | 2 mg |

Pharmaceutical example 13 Solid formulation

The powder in which the following prescription contained in 1 g was prepared according to the usual method.

| Prescription | The compound of Example 2 | 2 mg |
|---|---|---|
| | lactose | 996 mg |
| | Aerosil | 2 mg |

Pharmaceutical example 14 Solid formulation

The powder in which the following prescription contained in 1 g was prepared according to the usual method.

| Prescription | The compound of Example 27 | 2 mg |
|---|---|---|
| | lactose | 996 mg |
| | Aerosil | 2 mg |

Pharmaceutical example 15 Solid formulation

The powder in which the following prescription contained in 1 g was prepared according to the usual method.

| Prescription | The compound of Example 44 | 2 mg |
|---|---|---|
| | lactose | 996 mg |
| | Aerosil | 2 mg |

Pharmaceutical example 16 Solid formulation

The powder in which the following prescription contained in 1 g was prepared according to the usual method.

| Prescription | The compound of Example 58 | 2 mg |
|---|---|---|
| | lactose | 996 mg |
| | Aerosil | 2 mg |

Pharmaceutical example 17 Suppository

The suppository in which the following prescription contained in 2g of one suppository was prepared according to the usual method.

| Prescription | The compound of Example 2 | 2 mg |
|---|---|---|
| | suppository base | q.s. |

Pharmaceutical example 18 Suppository

The suppository in which the following prescription contained in 2 g of one suppository was prepared according to the usual method.

| Prescription | The compound of Example 27 | 2 mg |
|---|---|---|
| | suppository base | q.s. |

Pharmaceutical example 19 Suppository

The suppository in which the following prescription contained in 2 g of one suppository was prepared according to the usual method.

| Prescription | The compound of Example 44 | 2 mg |
|---|---|---|
| | suppository base | q.s. |

Pharmaceutical example 20 Suppository

The suppository in which the following prescription contained in 2 g of one suppository was prepared according to the usual method.

| Prescription | The compound of Example 58 | 2 mg |
|---|---|---|
| | suppository base | q.s. |

EFFECTS OF THE INVENTION

The compounds of the present invention are useful as reactivators of acetylcholinergic nervous system since they show eminent improvement effects on learning and memory disorders as well as have potent binding affinities for muscarinic receptors. Also, their safety margins are very wide.

The compounds of the present invention have superior effects that is not demonstrated in other known drugs, and also those have wider safety margins. Therefore those can be used as therapeutic drugs for senile dementia or as well as dementia and the like disease accompanied by mental-growth retardation, sequelae of encephalitis, cerebral palsy, cerebral apoplexy, cerebral arteriosclerosis, head injury and so forth.

We claim:

1. A compound of the formula

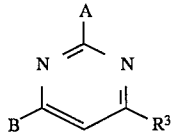

(I)

or a pharmacologically acceptable salt thereof wherein A and B are as follows:

When A represents

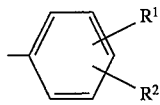

B represents methyl, trifluoromethyl, or tert-butyl; when B represents

A represents methyl, trifluoromethyl, or tert-butyl
wherein
$R^1$ and $R^2$ are the same or different and each is hydrogen, hydroxy, lower alkoxy, trifluoromethyl or halogen;
$R^3$ represents

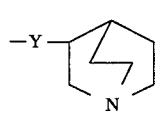

wherein Y represent O or NH, or

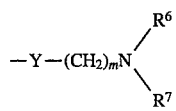

wherein Y represents O or NH, m is 2 or 3, and $R^6$ and $R^7$ form a 5 to 6 membered cyclic-amino group with the adjacent nitrogen atom, wherein said cyclic-amino group optionally includes an oxygen or sulfur atom, and said cyclic-amino group being unsubstituted or substituted by aryl with or without substituent(s), aralkyl with or without substituent(s) wherein the alkyl moiety thereof is lower alkyl, or aroyl with or without substituent(s).

2. A compound according to claim 1, wherein A represents

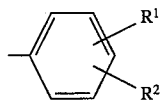

B is methyl,
wherein $R^1$ and $R^2$ are the same or different and each is hydrogen, halogen or alkoxy of 1 to 4 carbon atoms;
and further wherein $R^3$ is 3-quinuclidinyloxy, or piperidinoethoxy or piperidinopropoxy substituted with an aryl with or without substituent(s).

3. A compound according to claim 2, wherein $R^3$ is 3-quinuclidinyloxy, or piperidinoethoxy or piperidinopropoxy substituted with an aralkyl with or without substituent(s).

4. The compound according to claim 1, which is 4-(1-azabicyclo [2,2,2]octo-3-yloxy)-2-(4-fluorophenyl)-6-methylpyrimidine.

5. The compound according to claim 1, which is (R)-(−) 4-(1-azabicyclo [2,2,2]octo-3-yloxy) 2-(4-fluorophenyl)-6-methylpyrimidine.

6. The compound according to claim 1, which is 4-(1-azabicyclo [2,2,2]octo-3-yloxy)-2-(4-chlorophenyl)-6-methylpyrimidine.

7. The compound according to claim 1, which is (R)-(-)-4-(1-azabicyclo [2,2,2]octo-3-yloxy)-2-(4-chlorophenyl) 6-methylpyrimidine.

8. A method for treating dementia in animals and humans, which comprises administering to an animal or human in need thereof a therapeutically effective amount of a compound of the formula $$\underset{B}{\overset{A}{\underset{N}{\bigvee}}}\underset{R^3}{\overset{N}{\bigvee}}$$  (I)

or a pharmacologically acceptable salt thereof wherein A and B are as follows:

When A represents

[phenyl with R¹ and R²]

B represents methyl, trifluoromethyl, or tert-butyl; when B represents

[phenyl with R¹ and R²]

A represents methyl, trifluoromethyl, or tert-butyl wherein $R^1$ and $R^2$ are the same or different and each is hydrogen, hydroxy, lower alkoxy, trifluoromethyl or halogen;

$R^3$ represents

[—Y— cyclic amine structure]

wherein Y represents O or NH, $$-Y-(CH_2)_m N\overset{R^6}{\underset{R^7}{\diagdown}}$$

wherein Y represents O or NH, m is 2 or 3, $R^6$ and $R^7$ form a 5 to 6 membered cyclic-amino group with the adjacent nitrogen atom wherein these cyclic-amino groups optionally include oxygen or sulfur atom, and are unsubstituted or substituted by aryl with or without substituent(s), aralkyl with or without substituent(s) wherein the alkyl moiety is lower alkyl, or aroyl with or without substituent(s).

9. A method according to claim 8, wherein A represents

[phenyl with R¹ and R²]

B is methyl,
wherein $R^1$ and $R^2$ are the same or different and each is hydrogen, halogen or alkoxy of 1 to 4 carbon atoms;

and further wherein $R^3$ is 3-quinuclidinyloxy, or piperidinoethoxy or piperidinopropoxy substituted with an aryl with or without substituent(s).

10. A method according to claim 9, wherein $R^3$ is 3-quinuclidinyloxy, or piperidinoethoxy or piperidinopropoxy substituted with an aralkyl with or without substituent(s).

11. A method according to claim 8, wherein the compound is 4-(1-azabicyclo [2,2,2]octo-3-yloxy)-2-(4-fluorophenyl) 6-methylpyrimidine.

12. A method according to claim 8, wherein the compound is (R)-(-)-4-(1-azabicyclo [2,2,2]octo-3-yloxy) 2-(4-fluorophenyl)-6-methylpyrimidine.

13. A method according to claim 8, wherein the compound is 4-(1-azabicyclo [2,2,2]octo-3-yloxy)-2-(4-chlorophenyl) 6-methylpyrimidine.

14. A method according to claim 10, wherein the compound is (R)-(-)-4-(1-azabicyclo [2,2,2]octo-3-yloxy)-2-(4-chlorophenyl) 6-methylpyrimidine.

15. The method of claim 8, wherein $R^3$ represents $Y-(CH_2)_m N(R^6)(R^7)$, wherein $R^6$ and $R^7$ are lower alkyl or $R^6$ and $R^7$ together with the adjacent nitrogen atom form piperidino, and Y and m are as defined in claim 10.

16. The method of claim 8, wherein said compound is 4-[2-(N,N-diethylamino)ethoxy]-6-methyl-2-phenylpyrimidine or a pharmaceutically acceptable salt thereof.

17. The method of claim 8, wherein said compound is 2-(4-methoxyphenyl)-4-methyl-6-[2-(4-phenylpiperidino) ethoxy]-pyrimidine or a pharmaceutically acceptable salt thereof.

18. A pharmaceutical composition for treating dementia in animals and humans, which comprises a therapeutically effective amount of a compound of the formula $$\underset{B}{\overset{A}{\underset{N}{\bigvee}}}\underset{R^3}{\overset{N}{\bigvee}}$$  (I)

or a pharmacologically acceptable salt thereof wherein A and B are as follows:

When A represents

[phenyl with R¹ and R²]

B represents methyl, trifluoromethyl, or tert-butyl, when B represents

[phenyl with R¹ and R²]

A represents methyl, trifluoromethyl, or tert-butyl wherein $R^1$ and $R^2$ are the same or different and each is hydrogen, hydroxy, lower alkoxy, trifluoromethyl or halogen;

$R^3$ represents

[—Y— cyclic amine structure]

wherein Y represents O or NH, or

wherein Y represents O or NH, m is 2 or 3, and $R^6$ and $R^7$ form a 5 to 6 membered cyclic-amino group with the adjacent nitrogen atom wherein said cyclic-amino groups optionally include an oxygen or sulfur atom, and said cyclic amino group being unsubstituted or substituted by aryl with or without substituent(s), aralkyl with or without substituent(s) wherein the alkyl moiety is lower alkyl, or aroglor without substituent(s), in combination with a pharmaceutically acceptable inert diluent or carrier.

19. A pharmaceutical composition according to claim 18, wherein

A represents

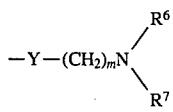

B is methyl, wherein $R^1$ and $R^2$ are the same or different and each is a hydrogen, halogen or alkoxy of 1 to 4 carbon atoms;

and further wherein $R^3$ is 3-quinuclidinyloxy, or piperidinoethoxy or piperidinopropoxy substituted with an aryl with or without substituent(s).

20. A pharmaceutical composition according to claim 19, wherein $R^3$ is 3-quinuclidinyloxy, or piperidinoethoxy or piperidinopropoxy substituted with an aralkyl with or without substituent(s).

21. A pharmaceutical composition according to claim 18, wherein the compound is 4-(1-azabicyclo [2,2,2]octo-3-yloxy)-2-(4-fluorophenyl)-6-methylpyrimidine.

22. A pharmaceutical composition according to claim 18, wherein the compound is (R)-(–)-4-(1-azabicyclo [2,2,2] octo-3-yloxy)-2-(4-fluorophenyl)-6-methylpyrimidine.

23. A pharmaceutical composition according to claim 18, wherein the compound is 4-(1-azabicyclo [2,2,2]octo-3-yloxy)-2-(4-chlorophenyl)-6-methylpyrimidine.

24. A pharmaceutical composition according to claim 18, wherein the compound is (R)-(–)-4-(1-azabicyclo [2,2,2] octo-3-yloxy)-2-(4-chlorophenyl)-6-methylpyrimidine.

* * * * *